United States Patent [19]

Egilmex

[11] Patent Number: 4,945,929
[45] Date of Patent: Aug. 7, 1990

[54] AEROSOL DEVICE SIMULATING A SMOKING ARTICLE

[75] Inventor: Nazli Egilmex, Southampton, England

[73] Assignee: British-American Tobacco Co., Ltd., London, England

[21] Appl. No.: 62,815

[22] Filed: Jun. 16, 1987

[30] Foreign Application Priority Data

Jun. 18, 1986 [GB] United Kingdom ............... 8614805

[51] Int. Cl.$^5$ .................... A24F 47/00; A61M 11/00; A61M 15/06
[52] U.S. Cl. ............... 131/273; 128/200.21; 128/202.21
[58] Field of Search ............. 131/273; 128/200.21, 128/202.21

[56] References Cited

U.S. PATENT DOCUMENTS 2,830,597  4/1958  Kummli .......................... 131/273
4,171,000  10/1979  Uhle ............................ 131/273
4,393,884  7/1983  Jacobs .......................... 131/273

Primary Examiner—V. Millin
Attorney, Agent, or Firm—Charles G. Lamb

[57] ABSTRACT

A nicotine dispensing aerosol device has nicotine and propellant storage containers connected to atomization nozzle from which a nicotine-aerosol spray can flow. A conical aerosol confining chamber extends from the nozzle, the cross-section of the chamber enlarging away from the nozzle. Large aerosol particles are removed by impaction on the upstream face of an impaction member, which member is located in the wider, outlet region of the aerosol confining chamber. A series of baffles are provided downstream of the impaction member, which baffles serve to produce a long, sinuous path for aerosol flow. The duration of the passage of the aerosol from the nozzle to the user is thereby increased, allowing more evaporation of the particulate phase of the aerosol. The device is, therefore, operable to dispense nicotine in an aerosol of a constitution which approximates that of tobacco smoke.

15 Claims, 1 Drawing Sheet

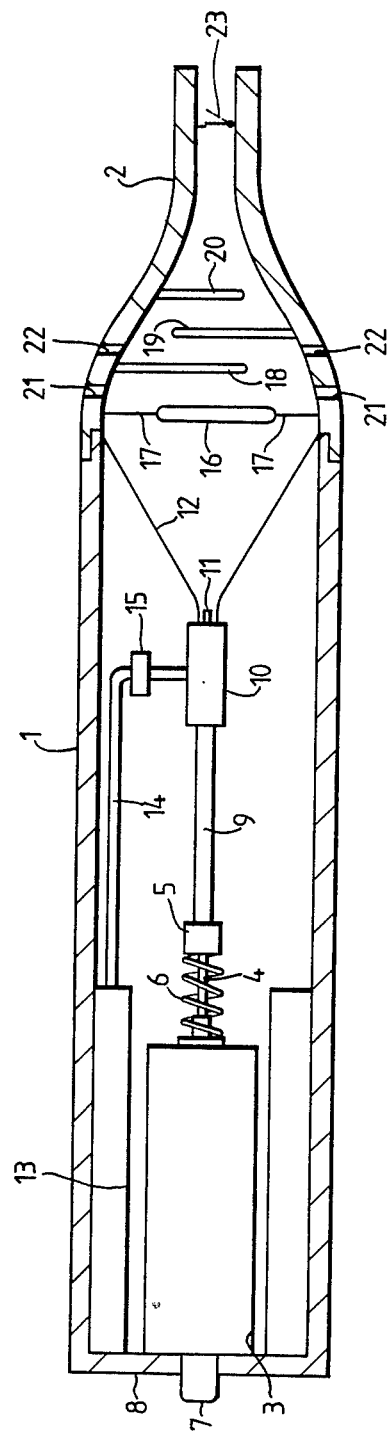

AEROSOL DEVICE SIMULATING A SMOKING ARTICLE

This invention relates to aerosol devices for dispensing nicotine, which devices are operable to simulate cigarettes, cigars or other smoking articles.

Inhaling devices have been heretofore proposed which, without the presence of combustion of the utilisation of heating means, can deliver nicotine vapour to the user. Such devices are disclosed in South African Patent Specification No. 69/7737 and in U.S. Pat. Nos. 2,860,638; 3,404,692 and 4,284,089. Although the user may derive a measure of satisfaction from such devices, the overall sensation registered lacks an attribute referred to by cigarette smokers as "mouthfullness". Mouthfullness relates to the texture and feel of tobacco smoke in the mouth. Tobacco smoke provides the degree of mouthfullness requisite to satisfy a smoker because of the fact that the smoke is an aerosol of specific constitution. The nicotine delivered by the devices of the above mentioned patent specifications is in vapor form only and it is for this reason that mouthfullness cannot be provided by such devices.

Proposals for non-combustion inhaling devices operable to dispense tobacco components in atomised form are disclosed in U.S. Pat. Nos. 2,051,030; 2,764,154; 2,809,634 and 4,393,884. However, none of these disclosures teaches the provision of nicotine in an aerosol of a constitution approximating the constitution of tobacco smoke.

It is an object of the present invention to provide a device operable to dispense nicotine in an aerosol of a constitution which approximates that of tobacco smoke more closely than would be possible using prior proposed devices. By reference to the constituion of an aerosol is meant the ratio of nicotine in the particulate and molecular (vapour) phases.

The present invention provides a nicotine dispensing aerosol device comprising nicotine-aerosol generating means, including storage means and nozzle means, said device further comprising an aerosol confining chamber having an inlet end and an outlet end, into which chamber said nozzle means is directed in the region of said inlet end, aerosol impaction means at which said nozzle means is directed and baffle means at that side of said impaction means further from said nozzle means.

Advantageously, the shape of the aerosol confining chamber should conform or approximate to the unconfined aerosol spray pattern produced by the nozzle means. Thus the chamber is suitably of substantially conical form, the cross-section of the chamber enlarging from the inlet to the outlet end.

The aerosol impaction means, which serves to remove by impaction large aerosol particles, suitably comprises a generally circular impaction face. The impaction face of the impaction means should be smaller than the transverse dimension assumed by the aerosol spray pattern at the location of the impaction means, whereby smaller particles and the vapour phase of the aerosol may flow freely past the impaction means. The impaction means may with advantage be located in the region of the outlet end of the conical chamber.

The baffle means provides for turbulence mixing which results in some evaporation from the particulate phase of the aerosol, thus increasing the vapour/particulate ratio of the aerosol. The baffle means may take the form of a plurality of interdigitated baffles defining a sinuous flow path for the aerosol. By imposing upon the aerosol a sinuous and thus lengthened flow path, the duration of the passage of the aerosol from the nozzle means to the user is increased and thus more time is available for evaporation from the particulate phase of the aerosol.

The above referred to components of devices according to the present invention may be contained within a generally tubular housing. Suitably, the housing comprises or has mounted with it a tapered mouthpiece. Air holes may be provided for the ingress of ventilation air to the aerosol flow path when the user exerts suction on the flow path.

If a device according to the present invention is intended for nasal inhalation of nicotine aerosol, the device may be provided with a nasal inhalation tube in communication with the aerosol flow path.

The outlet of the mouthpiece and/or nasal inhalation tube may be provided with valve means, flap valve means for example, resiliently urged to a closure position so as to prevent loss of nicotine from the device during periods of non-use thereof. If present, the ventilation air holes too are suitably provided with valve means for the same purpose.

Surfaces bounding the aerosol flow path may be lined with a material capable of absorbing any liquid nicotine deposited on the surfaces. By this expedient the drainage of liquid nicotine from the device is prevented. Moreover, during use of the device the liquid absorbed by the material may re-evaporate into the aerosol stream.

The nicotine-aerosol generating means may comprise metering means operable to meter a predetermined amount of nicotine to the nozzle means. The metering means may be adjustable, whereby the amount of nicotine delivered in an operation of the device may be varied.

The storage means of the nicotine-aerosol generating means may comprise a first container for nicotine and a second container for propellant, together with first and second feed means for the feed of the respective materials to the nozzle means. Other forms of aerosol generating means operable to atomise liquids and suitable for use in devices according to the present invention will readily occur to the skilled addressee.

The nicotine, which may be in free-base or salt form, is preferably contained in the storage means as a solution, although liquid free-base nicotine alone could be employed. There may if required be stored with the nicotine other tobacco components and/or non-tobacco materials, flavourants for example.

If there is used an aerosol generating device of a type in which the propellant is fed to the nozzle means, it is necessary that the propellant should be acceptable for ingestion. Air or nitrogen may, for example, be utilised.

In order that the present invention may be clearly understood and readily carried into effect, reference will now be made, by way of example, to the diagrammatic drawing hereof which shows an elevation with parts in axial section, of a nicotine inhaling device.

BRIEF DESCRIPTION OF THE DRAWINGS

The FIG. is a longitudinal cross-sectional view of the aerosol device of the invention.

The device shown in the drawing comprises a tubular housing 1 and a mouthpiece 2 secured to the housing 1 at the right-hand end as viewing the drawing. Within the housing 1 at the left-hand end thereof there is disposed an axially movable, cylindrical container 3 for compressed propellant gas. An outlet tube 4 is fixedly secured to and extends from the right-hand end of the container 3. At its end remote the container 3, the tube 4 is received in a valve 5. A coil spring 6 disposed between the container 3 and the valve 5 serves to urge the container 3 towards the leftmost position thereof, as shown in the drawing. When a button 7, secured to the container 3 and extending through an opening in an end wall 8 of the housing 1, is pressed, the container 3 is moved rightwardly against the force of the spring 6, whereby the tube 4 is caused to move rightwardly within the valve 5. In this manner the valve 5 is caused to open, whereby the tube 4 is placed in communication with a tube 9 which extends from the valve 5 to an atomization unit 10 comprising an atomising nozzle 11. As may be seen from the drawing, the nozzle 11 is disposed at the apex of a conical chamber 12 located at the right-hand end of the housing 1. At its wider outlet end the chamber 12 is fixedly secured to the housing 1.

Disposed within the housing 1 at the left-hand end thereof and being located about the container 3 is a container 13 of annular section which is intended to hold a solution comprising nicotine. Serving to intercommunicate the container 13 and the atomization unit 10 is a tube 14 in which is fitted a metering unit 15.

The components 3–7, 9–11 and 13–15 together constitute nicotine-aerosol generating means.

Positioned across the inlet end of the mouthpiece 2 and located close to the exit end of the conical chamber 12 is a disc shaped impaction member 16 of a diameter less than that of the mouthpiece 2 at said inlet end. Wire form support members 17 serve to support the member 16 concentrically of the mouthpiece 2, whereby there is an annular flow opening between the member 16 and the wall of the mouthpiece 2.

Behind the impaction member 16, that is to say to the right as viewing the drawing, there is disposed a series of interdigitated, transverse baffles each of which is secured to and extends inwardly from the wall of the mouthpiece 2. As shown, three baffles, designated 18–20, constitute the series, although a larger number could be utilised.

Reference numerals 21 and 22 designate arrays of ventilation air holes extending through the wall of the mouthpiece 2.

Each of these air holes may be provided with a flap valve which assumes a closed condition except when a user of the deviced exerts suction on the mouth-piece. If the air holes are provided with such flap valves, a further flap valve 23 is provided for obturating the flow passage of the mouthpiece 2 except when the device is in use.

In use of the nicotine inhaling device, the user, by pushing the button 7, causes the valve 5 to be opened, thereby permitting compressed propellant gas to flow from the container 3 to the atomization unit 10. In the unit 10 the propellant gas encounters nicotine solution in an amount determined by the metering unit 15. The gas propels the solution through the atomising nozzle 11, thus producing a nicotine aerosol spray in the chamber 12.

Large aerosol particles in a central region of the spray pattern are removed by impaction on impaction member 16. If these large particles remained in the aerosol they could give rise to adverse sensory effects. The smaller particles and the vapour phase of the aerosol flow around the member 16 and through the sinuous path defined by the baffles 18–20, in which path there takes place evaporation from the particulate to the vapour phase. The nicotine aerosol which flows to the user from the mouthpiece 2 is thus of a constitution providing for a balanced sensory perception including an adequate degree of mouthfullness.

Should the device be intended for nasal inhalation as well as for oral use, at the option of the user, there is provided a nasal inhalation tube in communication with the interior of the mouthpiece 2, preferably downstream of the baffles 18–20.

What is claimed is:

1. A nicotine dispensing aerosol device comprising nicotine-aerosol generating means and nozzle means for generating an aerosol spray of propellant gas and nicotine, including storage means for storing propellant gas and for storing nicotine, said device further comprising an aerosol confining chamber of substantially conical form having an inlet end and an outlet end into which chamber said nozzle means is directed in the region of said inlet end, for directing the aerosol from the nozzle toward aerosol impact means at the outlet end of the confining chamber and at which said nozzle means is directed for removing large particles from the nicotine-aerosol spray flowing from the confining chamber and baffle means at the side of said impact means further from said nozzle means for creating a turbulent flow of the nicotine-aerosol spray received by the baffle means from the impact means.

2. A device according to claim 1, wherein said storage means comprises nicotine-container means and feed means for the feed of nicotine from said container means to said nozzle means.

3. A device according to claim 1, wherein said storage means further comprises propellant-container means and feed means for the feed of propellant from said container means to said nozzle means.

4. A device according to claim 1, wherein nicotine in said storage means is in the form of a free-base solution or a nicotine salt solution.

5. A device according to claim 1, wherein nicotine in said storage means is in the form of liquid free-base nicotine.

6. A device according to claim 4 or 5, wherein other tobacco components and/or non-tobacco materials are stored with the nicotine.

7. A device according to claim 3, wherein said propellant is air or nitrogen.

8. A device according to claim 1, wherein the cross-section of said chamber enlarges from said inlet end to said outlet end.

9. A device according to claim 1, wherein said aerosol impaction means has an impaction face which is smaller than the transverse dimension assumed by the aerosol spray at the location of said impaction means.

10. A device according to claim 8, wherein said impaction means is located in the region of the outlet end of said aerosol confining chamber.

11. A device according to claim 1, wherein said baffle means is in the form of a plurality of interdigitated baffles defining a sinuous aerosol flow path.

12. A device according to claim 1, wherein said device is contained in a generally tubular housing.

13. A device according to claim 12, wherein said housing further comprises, or has mounted therewith, a tapered mouthpiece.

14. A device according to claim 1, wherein air holes are provided for the ingress of ventilation air to the aerosol flow path.

15. A nicotine dispensing aerosol device comprising nicotine-aerosol generating means and nozzle means for generating an aerosol spray of propellant gas and nicotine, including storage means for storing propellant gas and for storing nicotine, said device further comprising an aerosol confining chamber having an inlet end and an outlet end into which chamber said-nozzle means is directed in the region of said inlet end, for directing the aerosol from the nozzle toward aerosol impact means at the outlet end of the confining chamber, the nozzle means being directed at the aerosol impact means for removing large particles from the nicotine-aerosol spray, and baffle means at the side of said impact means further from said nozzle means for creating a turbulent flow of nicotine-aerosol spray received by the baffle means from the impact means, the baffle means being in the form of a plurality of interdigitated baffles defining a sinuous aerosol flow path.

* * * * *